United States Patent
Bock et al.

(10) Patent No.: US 9,090,553 B2
(45) Date of Patent: Jul. 28, 2015

(54) PROCESS FOR PREPARING CYCLOHEXANEPOLYCARBOXYLIC ACID DERIVATIVES HAVING A LOW PROPORTION OF BY-PRODUCTS

(71) Applicant: BASF SE, Ludwigshafen (DE)

(72) Inventors: Martin Bock, Ludwigshafen (DE); Boris Breitscheidel, Waldsee (DE)

(73) Assignee: BASF SE (DE)

( * ) Notice: Subject to any disclaimer, the term of this patent is extended or adjusted under 35 U.S.C. 154(b) by 37 days.

(21) Appl. No.: 14/045,178

(22) Filed: Oct. 3, 2013

(65) Prior Publication Data

US 2014/0100387 A1    Apr. 10, 2014

Related U.S. Application Data

(60) Provisional application No. 61/709,999, filed on Oct. 5, 2012.

(51) Int. Cl.
| | | |
|---|---|---|
| *C07C 61/09* | (2006.01) | |
| *C07C 69/75* | (2006.01) | |
| *C07C 51/36* | (2006.01) | |
| *C07C 67/303* | (2006.01) | |

(52) U.S. Cl.
CPC ............. *C07C 51/36* (2013.01); *C07C 61/09* (2013.01); *C07C 67/303* (2013.01); *C07C 2101/14* (2013.01)

(58) Field of Classification Search
None
See application file for complete search history.

(56) References Cited

U.S. PATENT DOCUMENTS

| | | |
|---|---|---|
| 3,027,398 A | 3/1962 | Foohey |
| 3,308,086 A | 3/1967 | Wartmann |
| 5,286,898 A | 2/1994 | Gustafson et al. |
| 5,319,129 A | 6/1994 | Gustafson et al. |
| 2002/0019559 A1 | 2/2002 | Brunner et al. |
| 2007/0255070 A1 | 11/2007 | Liu |
| 2008/0188601 A1 | 8/2008 | Grass et al. |
| 2012/0289747 A1 | 11/2012 | Königsmann et al. |
| 2012/0296111 A1 | 11/2012 | Königsmann et al. |

FOREIGN PATENT DOCUMENTS

| | | |
|---|---|---|
| DE | 1263296 B | 3/1968 |
| DE | 2823165 A1 | 11/1979 |
| EP | 0603825 A1 | 6/1994 |
| EP | 1042273 A1 | 10/2000 |
| EP | 1323700 A1 | 7/2003 |
| EP | 2316811 A1 | 5/2011 |
| WO | WO-94/29261 A1 | 12/1994 |
| WO | WO-2011082991 A2 | 7/2011 |

OTHER PUBLICATIONS

International Search Report for PCT/EP2013/70667 dated Feb. 10, 2014.

*Primary Examiner* — Yevegeny Valenrod
(74) *Attorney, Agent, or Firm* — Drinker Biddle & Reath LLP

(57) ABSTRACT

The present invention relates to a process for preparing at least one cyclohexanepolycarboxylic acid or a derivative thereof by bringing at least one corresponding benzenepolycarboxylic acid or a derivative thereof into contact with a hydrogen-comprising gas in the presence of at least one coated catalyst comprising an active metal selected from the group consisting of ruthenium, rhodium, palladium, platinum and mixes thereof, applied to a support material comprising silicon dioxide, where the pore volume of the support material is from 0.6 to 1.0 ml/g, determined by Hg porosimetry, the BET surface area is from 280 to 500 $m^2/g$, at least 90% of the pores present have a diameter of from 6 to 12 nm, and from 40 to 70% by weight of the active metal, based on the total amount of the active metal, are present in the catalyst coating up to a penetration depth of 200 μm, wherein the contacting is carried out at a superficial velocity of not more than 50 m/h.

10 Claims, No Drawings

PROCESS FOR PREPARING CYCLOHEXANEPOLYCARBOXYLIC ACID DERIVATIVES HAVING A LOW PROPORTION OF BY-PRODUCTS

CROSS-REFERENCE TO RELATED APPLICATIONS

This application claims the benefit of U.S. Provisional Application 61/709,999, filed Oct. 5, 2012, which is incorporate herein by reference.

The present invention relates to a process for preparing at least one cyclohexanepolycarboxylic acid or a derivative thereof by bringing at least one corresponding benzenepolycarboxylic acid or a derivative thereof into contact with a hydrogen-comprising gas in the presence of at least one coated catalyst comprising an active metal selected from the group consisting of ruthenium, rhodium, palladium, platinum and mixes thereof, applied to a support material comprising silicon dioxide, where the pore volume of the support material is from 0.6 to 1.0 ml/g, determined by Hg porosimetry, the BET surface area is from 280 to 500 $m^2/g$, at least 90% of the pores present have a diameter of from 6 to 12 nm, and from 40 to 70% by weight of the active metal, based on the total amount of the active metal, are present in the catalyst coating up to a penetration depth of 200 µm, wherein the contacting is carried out at a superficial velocity of not more than 50 m/h.

The present invention also provides selected representatives of the resulting cyclohexane-polycarboxylic acids or derivatives thereof, and also use of the resulting cyclohexane-polycarboxylic acids or derivatives thereof as plasticizers in plastics.

In U.S. Pat. No. 5,286,898 and U.S. Pat. No. 5,319,129, dimethyl terephthalate is hydrogenated over supported Pd catalysts admixed with Ni, Pt and/or Ru at temperatures of >140° C. and a pressure in the range from 50 to 170 bar to the corresponding dimethyl hexahydroterephthalate. In DE-A 28 23 165, aromatic carboxylic esters are hydrogenated over supported Ni, Ru, Rh, and/ or Pd catalysts to the corresponding cycloaliphatic carboxylic esters at from 70 to 250° C. and from 30 to 200 bar. U.S. Pat. No. 3,027,398 describes the hydrogenation of dimethyl terephthalate over supported Ru catalysts at from 110 to 140° C. and from 35 to 105 bar.

EP-A 0 603 825 relates to a process for preparing 1,4-cyclohexanedicarboxylic acid by hydrogenation of terephthalic acid using a supported palladium catalyst, with aluminum oxide, silicon dioxide or activated carbon being used as support. In the process described there, in particular, the solution comprising 1,4-cyclohexanedicarboxylic acid obtained in a first step is brought into contact with steam and impurities comprised in this solution are thereby extracted. However, this process can be employed only for acids, since there is a risk of hydrolysis when it is employed for derivatives such as esters, anhydrides, etc. EP 1 042 273 describes a process for hydrogenated polycarboxylic acid derivatives using a catalyst having macropores. The process displays a high space-time yield and a high selectivity.

Some cyclohexanepolycarboxylic acid derivatives and their use as plasticizers are likewise known from the prior art. Thus, dimethyl or diethyl cyclohexanedicarboxylate (DE-A 28 23 165), di(2-ethylhexyl)cyclohexane-1,2-dicarboxylate (DE-A 12 63 296) and diisononyl cyclohexane-1,2-dicarboxylate (EP 1 042 273) and their use as plasticizers in plastics have been described.

The disadvantage of the above-described preparative processes or the cyclohexane-polycarboxylic acid derivatives prepared by means of these processes is the high proportion of by-products in the end product, in particular a high proportion of hexahydrophthalide and isonomyl alcohol, which may require complicated additional purification. Due to this high proportion of by-products, the cyclohexanepolycarboxylic acid derivatives prepared by processes according to the prior art have disadvantageous use properties such as high volatility and poor compatibility with plastics, for example PVC, when used as plasticizers. As a result, the cyclohexanepolycarboxylic acid derivatives known from the prior art are therefore relatively unsuitable for sensitive applications in contact with human beings, e.g. for children's toys, food packaging or medical articles.

It was an object of the present invention to provide a process for hydrogenating benzenepolycarboxylic acid or derivatives thereof, by means of which the corresponding cyclohexanepolycarboxylic acids or derivatives thereof can be obtained in high purity, i.e. with a low proportion of secondary components, in particular with a low proportion of hexahydrophthalide and isonomyl alcohol.

A further object of the present invention was to provide selected cyclohexanepolycarboxylic acid derivatives which can be obtained by hydrogenation according to the invention of the corresponding benzenepolycarboxylic acid derivatives and are particularly suitable for use as plasticizers in plastics, in particular for sensitive applications in contact with human beings.

It has been found that cyclohexanepolycarboxylic acids or derivatives thereof having a reduced proportion of by-products, in particular hexahydrophthalide and isononanol, are obtained when the hydrogenation of the corresponding benzenepolycarboxylic acids or derivatives thereof, i.e. contacting of these compounds with a hydrogen-comprising gas, is carried out in the presence of a specific cated catalyst and at a superficial velocity of not more than 50 m/h.

The present invention accordingly provides a process for preparing at least one cyclohexane-polycarboxylic acid or a derivative thereof by bringing at least one corresponding benzenepolycarboxylic acid or a derivative thereof into contact with a hydrogen-comprising gas in the presence of at least one coated catalyst catalyst comprising an active metal selected from the group consisting of ruthenium, rhodium, palladium, platinum and mixes thereof, applied to a support material comprising silicon dioxide, where the pore volume of the support material is from 0.6 to 1.0 ml/g, determined by Hg porosimetry, the BET surface area is from 280 to 500 $m^2/g$, at least 90% of the pores present have a diameter of from 6 to 12 nm, and from 40 to 70% by weight of the active metal, based on the total amount of the active metal, are present in the catalyst coating up to a penetration depth of 200 µm, wherein the contacting is carried out at a superficial velocity of not more than 50 m/h.

The contacting according to the invention of the at least one cyclohexanepolycarboxylic acid or a derivative thereof with a hydrogen-comprising gas results in hydrogenation of these compounds to give the desired at least one cyclohexanepolycarboxylic acid or a derivative thereof. According to the invention, preferably only the aromatic system is hydrogenated, i.e. reduced, in order to obtain the corresponding saturated cycloaliphatic system, i.e. any further reducible groups present in the at least one substrate are, according to the invention, preferably not reduced.

In the process according to the invention for preparing at least one cyclohexanepolycarboxylic acid or a derivative thereof by bringing at least one corresponding benzenepolycarboxylic acid or a derivative thereof into contact with a hydrogen-comprising gas, at least one coated catalyst comprising an active metal selected from the group consisting of ruthenium, rhodium, palladium, platinum and mixes thereof applied to a support material comprising silicon dioxide, where the pore volume of the support material is from 0.6 to 1.0 ml/g, determined by Hg porosimetry, the BET surface area is from 280 to 500 m²/g, and at least 90% of the pores present have a diameter of from 6 to 12 nm, and from 40 to 70% by weight of the active metal, based on the total amount of the active metal, are present in the catalyst coating up to a penetration depth of 200 μm, is used.

Coated catalysts having an active metal on a support which are useful according to the invention are mentioned in WO2011/082991. The contents of WO2011/082991 are fully incorporated by reference into the present application.

The coated catalyst which is used according to the invention comprises an active metal selected from the group consisting of ruthenium, rhodium, palladium, platinum and mixtures thereof, preferably ruthenium, very particularly preferably ruthenium as sole active metal.

In the coated catalyst which is used according to the invention, the amount of the active metal is generally less than 1% by weight, preferably from 0.1 to 0.5% by weight, particularly preferably from 0.25 to 0.35% by weight, based on the total weight of the catalyst.

Coated catalysts are known per se to those skilled in the art. For the purposes of the present invention, the term "coated catalyst" means that the at least one active metal present, preferably ruthenium, is present predominantly in an outer shell of the support material.

In the coated catalyst which is used according to the invention, from 40 to 70% by weight, preferably from 50 to 60% by weight, of the active metal, based on the total amount of the active metal, are present in the shell of the catalyst to a penetration depth of 200 μm. In a particularly preferred embodiment, from 60 to 90% by weight, very particularly preferably from 70 to 80% by weight, of the active metal, based on the total amount of the active metal, is present in the shell of the catalyst to a penetration depth of 500 μm. The abovementioned data are determined by means of SEM (scanning electron microscopy) EPMA (electron probe microanalysis)—EDXS (energy dispersive X-ray spectroscopy) and represent average values. Further information regarding the abovementioned measurement methods and techniques are disclosed, for example, in *Spectroscopy in Catalysis* by J. W. Niemantsverdriet, VCH, 1995 or *Handbook of Microscopy* by S. Amelinckx et al. To determine the penetration depth of the active metal particles, polished sections of a plurality of catalyst particles (e.g. 3, 4 or 6) are prepared. The profiles of the active metal/Si concentration ratios are then determined by means of line scans. On each measurement line, a plurality of, for example from 15 to 20, measurement points at equal intervals are measured; the measurement spot size is about 10 μm*10 μm. After integration of the amount of active metal over the depth, the abundance of the active metal in a zone can be determined.

The amount of active metal, based on the concentration ratio of active metal to Si, at the surface of the coated catalyst is very particularly preferably from 2 to 25%, preferably from 4 to 10%, particularly preferably from 4 to 6%, determined by means of SEM EPMA - EDXS. The surface analysis is carried out by means of region analyses of regions of 800 μm*2000 μm and with an information depth of about 2 μm. The elemental composition is determined in % by weight (normalized to 100% by weight). The average concentration ratio (active metal/Si) is averaged over 10 measurement regions.

For the purposes of the present invention, the surface area of the coated catalyst is the external shell of the catalyst to a penetration depth of about 2 μm. This penetration depth corresponds to the information depth in the abovementioned surface analysis.

Very particular preference is given to a coated catalyst in which the amount of active metal, based on the weight ratio of active metal to Si (weight/weight in %), on the surface on the coated catalyst is from 4 to 6%, that to a penetration depth of 50 μm is from 1.5 to 3% and that in a region from 50 to 150 μm penetration depth is from 0.5 to 2%, determined by means of SEM EPMA (EDXS). The values specified are average values.

Furthermore, the size of the active metal particles preferably decreases with increasing penetration depth, determined by means of (FEG)-TEM analysis.

In the coated catalyst according to the invention, the active metal is preferably partially or entirely present in crystalline form. In preferred cases, very finely crystalline active metal can be detected in the shell of the coated catalyst according to the invention by means of SAD (selected area diffraction).

The coated catalyst which is preferred according to the invention can additionally comprise alkaline earth metal ions ($M^{2+}$), i.e. M=Be, Mg, Ca, Sr and/or Ba, in particular Mg and/or Ca, very particularly preferably Mg. The content of alkaline earth metal ion(s) ($M^{2+}$) in the catalyst is preferably from 0.01 to 1% by weight, in particular from 0.05 to 0.5% by weight, very particularly preferably from 0.1 to 0.25% by weight, in each case based on the weight of the silicon dioxide support material.

A significant constituent of the coated catalysts which are used according to the invention is the support material comprising silicon dioxide, preferably amorphous silicon dioxide. In this context, the term "amorphous" means that the proportion of crystalline silicon dioxide phases is less than 10% by weight of the support material. However, the support materials used for producing the catalysts can have surface structures formed by regular arrangement of pores in the support material.

Possible support materials are in principle amorphous silicon dioxide types which comprise at least 90% by weight of silicon dioxide, with the remaining at most 10% by weight, preferably not more than 5% by weight, of the support material also being able to be another oxidic material, e.g. MgO, CaO, $TiO_2$, $ZrO_2$ and/or $Al_2O_3$.

In a preferred embodiment of the invention, the support material is halogen-free, in particular chlorine-free, i.e. the content of halogen in the support material is generally less than 500 ppm by weight, e.g. in the range from 0 to 400 ppm by weight. Preference is thus given to a coated catalyst which comprises less than 0.05% by weight of halide (determined by ion chromatography), based on the total weight of the catalyst. The halide content of the support material is particularly preferably below the analytical detection limit. Preference is given to support materials which comprise silicon dioxide and have a specific surface area in the range from 280 to 500 m²/g, particularly preferably from 280 to 400 m²/g, very particularly preferably from 300 to 350 m²/g, (BET surface area in accordance with DIN 66131). They can either be of natural origin or have been synthetically produced. Examples of suitable amorphous support materials based on silicon dioxide are silica gels, kieselguhr, pyrogenic silicas and precipitated silicas. In a preferred embodiment of the invention, the catalysts have silica gels as support materials.

According to the invention, the pore volume of the support material is from 0.6 to 1.0 ml/g, preferably from 0.65 to 0.9 ml/g, for example from 0.7 to 0.8 ml/g, determined by Hg porosimetry (DIN 66133). In the coated catalyst which is preferred according to the invention, at least 90% of the pores present have a pore diameter of from 6 to 12 nm, preferably from 7 to 11 nm, particularly preferably from 8 to 10 nm. The pore diameter can be determined by methods known to those skilled in the art, for example by Hg porosimetry according to DIN 66133 or $N_2$ physisorption according to DIN 66131. In a preferred embodiment, at least 95%, particularly preferably at least 98%, of the pores present have a pore diameter of from 6 to 12 nm, preferably from 7 to 11 nm, particularly preferably from 8 to 10 nm.

In a preferred embodiment, no pores smaller than 5 nm are present in the coated catalyst which is preferred according to the invention. Furthermore, no pores which are larger than 25 nm, in particular larger than 15 nm, are present in the coated catalyst which is preferred according to the invention. In this context, "no pores" means that no pores having these diameters are found by customary measurement methods, for example Hg porosimetry according to DIN 66133 or $N_2$ physisorption according to DIN 66131. Within measurement accuracy of the analytical method used, preferably no macropores but only mesopores are present in the coated catalyst which is used according to the invention.

In the coated catalyst which is preferred according to the invention, particular preference is given to using shaped bodies composed of the support material which can be obtained, for example, by extrusion, ram extrusion or tableting and can have, for example, the shape of spheres, pellets, cylinders, rods, rings or hollow cylinders, stars and the like, particularly preferably spheres. The dimensions of these shaped bodies are usually in the range from 0.5 mm to 25 mm. Preference is given to using catalyst spheres having sphere diameters of from 1.0 to 6.0 mm, particularly preferably from 2.5 to 5.5 mm. In the coated catalyst which is preferred according to the invention, the dispersity of the active metal is preferably from 30 to 60%, particularly preferably from 30 to 50%. Methods of measuring the dispersity of the active metal are known per se to those skilled in the art, for example pulse chemisorption, with the determination of the noble metal dispersion (specific metal surface area, crystallite size) being carried out by the CO pulse method (DIN 66136(1-3)).

In the coated catalyst which is preferred according to the invention, the surface area of the active metal is preferably from 0.2 to 0.8 $m^2/g$, particularly preferably from 0.3 to 0.7 $m^2/g$. Methods of measuring the surface area of the active metal are known per se to those skilled in the art.

The coated catalysts which are preferred according to the invention are produced, for example, by firstly impregnating the support material one or more times with a solution comprising a precursor compound of the active metal, drying the solid obtained and subsequently reducing it. The individual process steps are known per se to those skilled in the art and are described in WO 2011/082991.

Carrying Out the Process:

It is important for the purposes of the invention that the contacting of the at least one benzene-polycarboxylic acid or a derivative thereof with the hydrogen-comprising gas, i.e. the hydrogenation of the at least one benzenepolycarboxylic acid or a derivative thereof, in the process of the invention is carried out at a superficial velocity of not more than 50 m/h in the first reactor; the process of the invention is particularly preferably carried out at a superficial velocity of more than 40 m/h. The process of the invention is generally carried out at a superficial velocity of at least 20 m/h.

The superficial velocity is, for the purposes of the invention, defined as follows:

$$\text{Superficial velocity} = V(\text{feed})/(A(\text{1st reactor})*t),$$

where V(feed to 1st reactor) is the sum of the volume of the starting material, i.e. the at least one benzenepolycarboxylic acid or a derivative thereof, and the solvent, i.e. the product circulated after passing through the 1st reactor, in each case in $m^3$, A(reactor) is the cross-sectional area of the reactor in $m^2$ and t is the time in hours for the V(feed) to pass through the cross-sectional area A. Superficial velocity is therefore a measure of the flow velocity in the reactor.

In the context of the invention, the contacting, i.e. the hydrogenation, is generally carried out at a temperature of 50 to 250° C., preferably from 70 to 180° C. The pressures used here are generally above 10 bar, preferably in the range from 20 to 80 bar, particularly preferably in the range from 30 to 50 bar.

The present invention therefore preferably provides the process of the invention in which the contacting, i.e. the hydrogenation is carried out at a temperature of from 50 to 250° C., preferably from 70 to 180° C., and a pressure above 10 bar, preferably in the range from 20 to 80 bar, particularly preferably in the range from 30 to 50 bar.

The process of the invention can be carried out either continuously or batchwise, with the continuous process being preferred.

The process of the invention is preferably carried out in downflow reactors or in the flooded mode in fixed-bed operation. The hydrogen-comprising gas can be passed over the catalyst either in cocurrent with the solution of the starting material to be hydrogenated or in countercurrent. The hydrogenation can also be carried out batchwise.

In the continuous process, the amount of the at least one benzenepolycarboxylic acid or a derivative thereof to be hydrogenated is preferably from 0.05 to 3 kg per liter of catalyst per hour, more preferably from 0.1 to 1 kg per liter of catalyst per hour.

As hydrogenation gases, it is possible to use any gases which comprise hydrogen in free form and do not have any harmful amounts of catalyst poisons such as CO. For example, it is possible to use reformer offgases. Preference is given to using pure hydrogen as hydrogenation gas.

The process of the invention can be carried out in the absence or presence of a solvent or diluent, i.e. it is not necessary to carry out the process in solution.

However, a solvent or diluent is preferably used. As solvent or diluent, it is possible to use any suitable solvent or diluent. The choice is not critical as long as the solvent or diluent used is able to form a homogeneous solution with the at least one benzenepolycarboxylic acid or a derivative thereof.

For example, the solvent or diluent can also comprise water. For example, a solvent or diluent is selected from the group consisting of straight-chain or cyclic ethers, for example tetrahydrofuran or dioxane, aliphatic alcohols in which the alkyl radical preferably has from 1 to 10 carbon atoms, in particular from 3 to 6 carbon atoms, for example i-propanol, n-butanol, i-butanol, n-hexanol and mixtures thereof.

The amount of solvent or diluent used is not restricted in any particular way and can be chosen freely according to requirements, but preference is given to amounts which lead to a from 10 to 70% strength by weight solution of the at least one benzenepolycarboxylic acid or derivative thereof provided for the hydrogenation.

In the process of the invention, the product formed in the hydrogenation, i.e. the corresponding cyclohexanepolycarboxylic acid or a derivative thereof, is particularly preferably used as solvent, optionally in addition to other solvents or diluents. In any case, part of the product formed in the process can be mixed into the benzenepolycarboxylic acid or derivative thereof still to be hydrogenated. Based on the weight of the compound provided for the hydrogenation, preference is given to mixing in from 1 to 30 times, particularly preferably from 5 to 20 times, in particular from 5 to 10 times, the amount of reaction product as solvent or diluent.

The at least one cyclohexanepolycarboxylic acid or derivative thereof obtained according to the invention is preferably a compound of the formula (I),

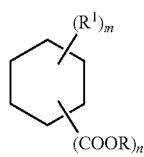

where
R$^1$ is C$_1$-C$_4$-alkyl,
m is 0, 1, 2 or 3,
n is 2, 3 or 4 and
R is hydrogen, C$_4$-C$_2$-alkyl.

To obtain these compounds of the general formula (I), the corresponding aromatic compounds of the general formula (II):

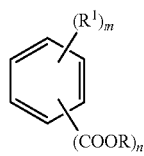

where
R$^1$ is C$_1$-C$_4$-alkyl,
m is 0, 1, 2 or 3,
n is 2, 3 or 4 and
R is hydrogen, C$_4$-C$_{12}$-alkyl,
are used according to the invention as starting materials.

The meanings of R$^1$, R, m and n in the general formulae (I) and (II) are discussed jointly below; a person skilled in the art will be aware that the compounds of the formulae (I) and (II) differ in the number of ring hydrogens.

When m is 2 or 3, the radicals R$^1$ can be identical or different. The C$_1$-C$_4$-alkyl groups can be linear or branched. When R$^1$ is an alkyl group, it is preferably methyl, ethyl, n-propyl-, i-propyl, n-butyl, i-butyl, sec-butyl or tert-butyl. m is preferably 0, i.e. there are no C$_1$-C$_4$-alkyl substituents present but exclusively hydrogen atoms, so that an aromatic benzene ring (general formula II) or a saturated cyclohexyl ring (general formula (I)) is present.

The n radicals R can be identical or different. When R is hydrogen, the compound is a cyclohexanepolycarboxylic acid or benzenepolycarboxylic acid. The C$_4$-C$_{12}$-alkyl groups can be linear or branched. R is preferably C$_6$-C$_{12}$-alkyl, very particularly preferably C$_8$-C$_{10}$-alkyl. Examples of such alkyl groups are n-butyl, i-butyl, sec-butyl or tert-butyl, n-pentyl, n-hexyl, n-octyl, 2-ethylhexyl, n-nonyl, isononyl, n-decyl, isodecyl, n-undecyl, isoundecyl, n-dodecyl, isododecyl, n-tridecyl, isotridecyl, stearyl and n-eicosyl.

If anhydrides of the at least one benzenepolycarboxylic acid or a derivative thereof are used according to the invention, two carboxylic acid groups are joined to one another with elimination of one molecule of H$_2$O. Here, the two carboxylic acid groups can be present in one molecule (intramolecular) or two molecules (intermolecular). This applies to the starting materials of the general formula (II) and to the products of the general formula (I) and is known to those skilled in the art.

The alkyl groups can each be single isomers of the alkyl groups mentioned or be mixtures of different alkyl groups. The different alkyl groups can be different isomers having the same number of carbon atoms and/or alkyl groups which have a different number of carbon atoms.

The cyclohexanepolycarboxylic acids or derivatives thereof of the general formula (I) obtained according to the invention are, in particular, monoesters, diesters, triesters, tetraesters and anhydrides of the cyclohexanepolycarboxylic acids. Preference is given to all carboxylic acid groups being esterified. The esters used are alkyl esters, with preferred alkyl groups R having been mentioned above.

According to the invention, preference is given to cyclohexanepolycarboxylic acid derivatives selected from the group consisting of ring-hydrogenated monoalkyl and dialkyl esters of phthalic acid, isophthalic acid and terephthalic acid, ring-hydrogenated monoalkyl, dialkyl and trialkyl esters of trimellitic acid, of trimesic acid and of hemimellitic acid or monoalkyl, dialkyl, trialkyl and tetraalkyl esters of pyromellitic acid, where the alkyl groups R are as defined above.

The benzenepolycarboxylic acids which are preferably used according to the invention are, in particular, selected from the group consisting of phthalic acid, isophthalic acid, terephthalic acid, trimellitic acid, trimesic acid, hemimellitic acid, pyromellitic acid and mixtures thereof. Very particular preference is given to using phthalic acid. The abovementioned acids are commercially available.

Preference is also given according to the invention to using benzenepolycarboxylic esters of the general formula (II). These are obtained, for example, by reacting at least one benzene-polycarboxylic acid selected from the group consisting of phthalic acid, isophthalic acid, terephthalic acid, trimellitic acid, trimesic acid, hemimellitic acid, pyromellitic acid and mixtures thereof with appropriate alcohols R—OH.

As alcohols, preference is given to using the alcohols corresponding to the radicals R of the cyclohexanepolycarboxylic acid derivatives of the formula I.

Preference is thus given to using linear or branched alcohols having C$_4$-C$_{12}$-alkyl radicals. The alcohols used for esterification with the benzenepolycarboxylic acids can in each case be the individual isomers of the alcohols corresponding to the abovementioned radicals R or mixtures of different alcohols having isomeric alcohol radicals having the same number of carbon atoms and/or mixtures of different alcohols having different numbers of carbon atoms.

The alcohols or alcohol mixtures suitable for reaction with the benzenepolycarboxylic acids can be prepared by all methods known to those skilled in the art. Suitable processes for preparing alcohols or process steps employed in the preparation of alcohols are, for example:
hydroformylation with subsequent hydrogenation of the aldehydes formed, for example as disclosed in WO 92/13818;
hydrogenation of aldol products, for example as disclosed in DE-A 102 51 311;
hydration of alkenes, for example as disclosed in U.S. Pat. No. 5,136,108;
hydrogenation of carboxylic acids and carboxylic esters, in particular fatty acids and fatty acid esters, for example as disclosed in U.S. Pat. No. 5,463,143;
hydrogenation of unsaturated alcohols or of carbonyl compounds, for example as disclosed in EP-A 0 394 842;

hydrogenation of epoxides, for example as disclosed in GB-A 879 803;

processes comprising a telomerization step, for example as disclosed in U.S. Pat. No. 3,091,628;

processes comprising an isomerization step, for example as disclosed in DE-A 42 28 887;

hydrolysis of sulfates, for example as disclosed in GB-A 1,165,309;

reaction with dienes with amines, for example as disclosed in DE-A 44 31 528;

enzymatic preparation of alcohols, for example as disclosed in WO 93/24644;

selective hydrogenation of dienes, for example as disclosed in U.S. Pat. No. 3,203,998;

preparation of alcohols from nitriles, for example as disclosed in EP-A 0 271 092;

preparation of alcohols by reaction of alkynes, for example as disclosed in RU 205 9597-C1; and hydrogenolysis of substituted tetrahydropyrans, for example as disclosed in GB 1,320,188.

A person skilled in the art will know of further processes for preparing alcohols, which can likewise be used for alcohols or alcohol mixtures suitable for esterification with benzenepolycarboxylic acids.

Alcohols which are preferably used are, as mentioned above, alcohols which have $C_4$-$C_{12}$-alkyl radicals. In particular, the relatively long-chain $C_5$-$C_{12}$-alcohols or alcohol mixtures comprising these alcohols are particularly preferably prepared by catalytic hydroformylation (also referred to as the oxo process) of olefins and subsequent hydrogenation of the aldehydes formed.

Suitable hydroformylation processes are known to those skilled in the art and are disclosed in the abovementioned documents. The alcohols and alcohol mixtures disclosed in the documents cited can be reacted with the abovementioned benzenepolycarboxylic acids to form the desired alkyl benzenepolycarboxylates or benzenepolycarboxylic ester mixtures.

$C_5$-Alcohols or mixtures comprising $C_5$-alcohols, particularly preferably n-pentanol, can be prepared, for example, by hydroformylation of butadiene in the presence of an aqueous solution of a rhodium compound and a phosphine as catalyst. Such a process is disclosed, for example, in EP-A 0 643 031.

Suitable $C_7$-alcohol mixtures which can be used for esterification with the benzene-polycarboxylic acids are disclosed, for example, in JP-A 2000/319 444. The $C_7$-alcohol mixture is prepared by hydroformylation with subsequent hydrogenation of the aldehydes formed.

Mixtures comprising $C_8$-alcohols and processes for preparing them are disclosed, for example, in GB-A 721 540, in which a process for preparing isooctyl alcohols from heptenes by means of hydroformylation and subsequent hydrogenation is described. An example of a further document which discloses the preparation of $C_7$-alcohols or mixtures comprising these alcohols is DE-A 195 30 414.

$C_9$-Alcohols or mixtures comprising $C_9$-alcohols are preferably prepared by dimerization of butenes, hydroformylation of the octenes obtained and subsequent hydrogenation of the $C_9$-aldehyde obtained.

Suitable processes and $C_9$-alcohol-comprising mixtures are disclosed, for example, in WO 92/13818.

$C_{10}$-Alcohols and mixtures comprising these alcohols are disclosed, for example, in WO 2003/66642.

$C_{12}$-Alcohols and mixtures comprising $C_{12}$-alcohols, in particular trimethylnonanol, and a process for the preparation thereof are disclosed, for example, in WO 98/03462.

According to the invention, particular preference is given to obtaining dialkyl esters of the abovementioned cyclohexanedicarboxylic acids, in particular 1,2-, 1,3- or 1,4-dialkyl esters and very particularly preferably 1,2-dialkyl esters. Here, it is possible to obtain dialkyl esters or use the corresponding dialkyl benzenedicarboxylates in which both ester groups of the dialkyl ester bear the same alkyl radicals and also ester groups in which the two ester groups of the dialkyl ester bear different alkyl groups. Examples of mixed and unmixed dialkyl esters have been mentioned above. Furthermore, it is possible for the alkyl groups to have the same number of carbon atoms but be linear or have a variety of branching and thus form isomer mixtures. Such isomer mixtures can also be used when the number of carbon atoms in the alkyl groups of the dialkyl ester is different. The proportion of the various isomers of the alkyl groups is generally determined by the composition of the alcohols used for esterification of the benzenedicarboxylic acids which are, after esterification, hydrogenated according to the invention to form the cyclohexanedicarboxylic esters. Suitable alcohol mixtures have been mentioned above. For the purposes of the present application, linear or branched alkyl radicals having a particular number of carbon atoms include not only the respective individual isomers but also isomer mixtures whose composition is, as mentioned above, determined by the composition of the alcohols used for esterification of the benzenedicarboxylic acids.

For the purposes of the present application, linear alkyl radicals can be both exclusively linear alkyl radicals and also mixtures of alkyl radicals which are predominantly linear.

If the alkyl radicals R of the cyclohexanepolycarboxylic esters are $C_4$-alkyl radicals, these are obtained by reaction of the benzenepolycarboxylic acids of the formula (II) in which R is hydrogen with n-butanol, isobutanol, sec-butanol or tert-butanol. For the preparation of benzenepolycarboxylic esters in which R is a $C_4$-radical, it is possible to use mixtures of the respective butanols mentioned or individual isomers. Preference is given to using individual isomers of butanol. The preparation of the abovementioned $C_4$-alcohols is known to those skilled in the art.

If the alkyl radicals R of the cyclohexanepolycarboxylic ester are $C_5$-$C_{12}$-alkyl radicals, preference is given to using $C_5$-$C_{12}$-alcohols having a degree of branching (ISO index) of generally from 0.10 to 4, preferably from 0.5 to 3, particularly preferably from 0.8 to 2 and in particular from 1 to 1.5, i.e. the respective alcohols are generally mixtures of various isomers.

Very particular preference is given to using $C_9$-alcohol mixtures having an ISO index of from 1 to 2.5, in particular nonanol mixtures having an ISO index of 1.25 or 1.6. The ISO index is a dimensionless parameter which was determined by means of gas chromatography.

Method: Capillary GC

Apparatus: Capillary gas chromatograph with autosampler, split/splitless injection system and flame ionization detector (FID)

Chemicals: MSTFA (N-methyl-N-trimethylsilyltrifluoroacetamide) appropriate comparative substances for determining the retention times sample preparation: 3 drops of the sample are added to 1 ml of MSTFA and maintained at 80° C. for 60 minutes GC conditions: Capillary column Ultra-1, length 50 m, internal diameter 0.25 mm, film thickness 0.1 micron, carrier gas helium, Column admission pressure 200 psi constant, Split 80 ml/min, Septum flushing 3 ml/min, Oven temperature 120° C., 25 min, isothermal, Injector temperature 250° C.,
Detector temperature 250° C. (FID),
Injection volume 0.5 microliter
Calculation: The procedure for calculating the Iso index can be seen from the following table
Table with illustrative calculation of the Iso index:

| Component | Name | Branching | Proportion in % by area | Index |
|---|---|---|---|---|
| 1 | 2-Ethyl-2-methyl-1-hexanol | 2 | 1.00 | 0.0200 |
| 2 | 2-Ethyl-4-methyl-1-hexanol | 2 | 1.00 | 0.0200 |
| 3 | 2-Ethyl-4-methyl-1-hexanol | 2 | 1.00 | 0.0200 |
| 4 | 2-Propyl-3-methyl-1-pentanol | 2 | 1.00 | 0.0200 |
| 5 | 2-Propyl-1-hexanol | 1 | 1.00 | 0.0100 |
| 6 | 2,5-Dimethyl-1-heptanol | 2 | 1.00 | 0.0200 |
| 7 | 2,3-Dimethyl-1-heptanol | 2 | 1.00 | 0.0200 |
| 8 | 2,3,4-Trimethyl-1-hexanol | 3 | 1.00 | 0.0300 |
| 9 | 2-Ethyl-1-heptanol | 1 | 1.00 | 0.0100 |
| 10 | 3-Ethyl-4-methyl-1-hexanol | 2 | 82.00 | 1.6400 |
| 11 | 3-Ethyl-1-heptanol | 1 | 1.00 | 0.0100 |
| 12 | 2-Methyl-1-octanol | 1 | 1.00 | 0.0100 |
| 13 | 4,5-Dimethyl-1-heptanol | 2 | 1.00 | 0.0200 |
| 14 | 4,5-Dimethyl-1-heptanol | 2 | 1.00 | 0.0200 |
| 15 | 4-Methyl-1-octanol | 1 | 1.00 | 0.0100 |
| 15a | 7-Methyl-1-octanol | 1 | 1.00 | 0.0000 |
| 16 | 6-Methyl-1-octanol | 1 | 1.00 | 0.0100 |
| 17 | 1-Nonanol | 0 | 1.00 | 0.0000 |
|  | Unknown component | 2 | 1.00 | 0.0200 |
|  | Total |  | 99.00 | 1.9000 |
|  |  |  | Iso index: | 1.9200 |

The $C_5$-$C_{12}$-alcohols are prepared by the abovementioned processes. To prepare benzenepolycarboxylic esters in which R is a $C_9$-alkyl radical, particular preference is given to using a nonanol mixture in which from 0 to 20% by weight, preferably from 0.5 to 18% by weight, particularly preferably from 6 to 16% by weight, of the nonanol mixture have no branching, from 5 to 90% by weight, preferably from 10 to 80% by weight, particularly preferably from 45 to 75% by weight, have one branching point, from 5 to 70% by weight, preferably from 10 to 60% by weight, particularly preferably from 15 to 35% by weight, have two branching points, from 0 to 10% by weight, preferably from 0 to 8% by weight, particularly preferably from 0 to 4% by weight, have three branching points and from 0 to 40% by weight, preferably from 0.1 to 30% by weight, particularly preferably from 0.5 to 6.5% by weight, are other components. Other components are generally nonanols having more than three branching points, decanols or octanols, with the sum of the components mentioned being 100% by weight.

The present invention therefore preferably provides the process of the invention in which the at least one derivative of the benzenepolycarboxylic acid is a monoester, diester, triester, tetraester or anhydride of the benzenepolycarboxylic acid. Preference is given to all carboxylic acid groups being esterified. The esters used are alkyl esters, with preferred alkyl groups R having been mentioned above.

The present invention more preferably provides the process of the invention in which the at least one derivative of a benzenepolycarboxylic acid is a monoester, diester, triester or tetraester of the benzenepolycarboxylic acid, which ester has been obtained by reaction with a nonanol mixture in which from 0 to 20% by weight, preferably from 0.5 to 18% by weight, particularly preferably from 6 to 16% by weight, of the nonanol mixture have no branching, from 5 to 90% by weight, preferably from 10 to 80% by weight, particularly preferably from 45 to 75% by weight, have one branching point, from 5 to 70% by weight, preferably from 10 to 60% by weight, particularly preferably from 15 to 35% by weight, have two branching points, from 0 to 10% by weight, preferably from 0 to 8% by weight, particularly preferably from 0 to 4% by weight, have three branching points and from 0 to 40% by weight, preferably from 0.1 to 30% by weight, particularly preferably from 0.5 to 6.5% by weight, are other components, with the sum of the components mentioned being 100% by weight.

A particularly preferred embodiment of a nonanol mixture used for preparing benzenepolycarboxylic acid derivatives which are preferably used has the following composition:
from 1.73 to 3.73% by weight, preferably from 1.93 to 3.53% by weight, particularly preferably from 2.23 to 3.23% by weight, of 3-ethyl-6-methylhexanol;
from 0.38 to 1.38% by weight, preferably from 0.48 to 1.28% by weight, particularly preferably from 0.58 to 1.18% by weight, of 2,6-dimethylheptanol;
from 2.78 to 4.78% by weight, preferably from 2.98 to 4.58% by weight, particularly preferably from 3.28 to 4.28% by weight, of 3,5-dimethylheptanol;
from 6.30 to 16.30% by weight, preferably from 7.30 to 15.30% by weight, particularly preferably from 8.30 to 14.30% by weight, of 3,6-dimethylheptanol;
from 5.74 to 11.74% by weight, preferably from 6.24 to 11.24% by weight, particularly preferably from 6.74 to 10.74% by weight, of 4,6-dimethylheptanol;
from 1.64 to 3.64% by weight, preferably from 1.84 to 3.44% by weight, particularly preferably from 2.14 to 3.14% by weight, of 3,4,5-trimethylhexanol;
from 1.47 to 5.47% by weight, preferably from 1.97 to 4.97% by weight, particularly preferably from 2.47 to 4.47% by weight, of 3,4,5-trimethylhexanol, 3-methyl-4-ethylhexanol and 3-ethyl-4-methyl hexanol;
from 4.00 to 10.00% by weight, preferably from 4.50 to 9.50% by weight, particularly preferably from 5.00 to 9.00% by weight, of 3,4-dimethylheptanol;
from 0.99 to 2.99% by weight, preferably from 1.19 to 2.79% by weight, particularly preferably from 1.49 to 2.49% by weight, of 4-ethyl-5-methylhexanol and 3-ethylheptanol;
from 2.45 to 8.45% by weight, preferably from 2.95 to 7.95% by weight, particularly preferably from 3.45 to 7.45% by weight, of 4,5-dimethylheptanol and 3-methyloctanol;
from 1.21 to 5.21% by weight, preferably from 1.71 to 4.71% by weight, particularly preferably from 2.21 to 4.21% by weight, of 4,5-dimethylheptanol;
from 1.55 to 5.55% by weight, preferably from 2.05 to 5.05% by weight, particularly preferably from 2.55 to 4.55% by weight, of 5,6-dimethylheptanol;
from 1.63 to 3.63% by weight, preferably from 1.83 to 3.43% by weight, particularly preferably from 2.13 to 3.13% by weight, of 4-methyloctanol;
from 0.98 to 2.98% by weight, preferably from 1.18 to 2.78% by weight, particularly preferably from 1.48 to 2.48% by weight, of 5-methyloctanol;
from 0.70 to 2.70% by weight, preferably from 0.90 to 2.50% by weight, particularly preferably from 1.20 to 2.20% by weight, of 3,6,6-trimothylhexanol;
from 1.96 to 3.96% by weight, preferably from 2.16 to 3.76% by weight, particularly preferably from 2.46 to 3.46% by weight, of 7-methyloctanol;
from 1.24 to 3.24% by weight, preferably from 1.74 to 2.74% by weight, particularly preferably from 1.74 to 2.74% by weight, of 6-methyloctanol; from 0.1 to 3% by weight, preferably from 0.2 to 2% by weight, particularly preferably from 0.3 to 1% by weight, of n-nonanol;

from 25 to 35% by weight, preferably from 28 to 33% by weight, particularly preferably from 29 to 32% by weight, of other alcohols having 9 and 10 carbon atoms;
where the total sum of the components mentioned is 100% by weight.

Such an isononanol mixture esterified with phthalic acid is present in the diisononyl phthalate of CAS No. 68515-48-0, from which the diisononyl cyclohexane-1,2-dicarboxylate having a corresponding isononyl component can be produced by hydrogenation of the aromatic ring by means of the process of the invention. Such isononanol mixtures can be obtained via zeolite-catalyzed oligomerization of $C_2$-, $C_3$- and $C_4$-olefin mixtures, known as the polygas process, isolation of a $C_8$ fraction from the oligomerizate and subsequent hydroformylation and hydrogenation thereof.

A further particularly preferred embodiment of a nonanol mixture used for preparing benzenepolycarboxylic acid derivatives which are preferably used has the following composition:
from 6.0 to 16.0% by weight, preferably from 7.0 to 15.0% by weight, particularly preferably from 8.0 to 14.0% by weight, of n-nonanol;
from 12.8 to 28.8% by weight, preferably from 14.8 to 26.8% by weight, particularly preferably from 15.8 to 25.8% by weight, of 6-methyloctanol;
from 12.5 to 28.8% by weight, preferably from 14.5 to 26.5% by weight, particularly preferably from 15.5 to 25.5% by weight, of 4-methyloctanol;
from 3.3 to 7.3% by weight, preferably from 3.8 to 6.8% by weight, particularly preferably from 4.3 to 6.3% by weight, of 2-methyloctanol;
from 5.7 to 11.7% by weight, preferably from 6.3 to 11.3% by weight, particularly preferably from 6.7 to 10.7% by weight, of 3-ethylheptanol;
from 1.9 to 3.9% by weight, preferably from 2.1 to 3.7% by weight, particularly preferably from 2.4 to 3.4% by weight, of 2-ethylheptanol;
from 1.7 to 3.7% by weight, preferably from 1.9 to 3.5% by weight, particularly preferably from 2.2 to 3.2% by weight, of 2-propylhexanol;
from 3.2 to 9.2% by weight, preferably from 3.7 to 8.7% by weight, particularly preferably from 4.2 to 8.2% by weight, of 3,5-dimethylheptanol; from 6.0 to 16.0% by weight, preferably from 7.0 to 15.0% by weight, particularly preferably from 8.0 to 14.0% by weight, of 2,5-dimethyl-heptanol;
from 1.8 to 3.8% by weight, preferably from 2.0 to 3.6% by weight, particularly preferably from 2.3 to 3.3% by weight, of 2,3-dimethylheptanol;
from 0.6 to 2.6% by weight, preferably from 0.8 to 2.4% by weight, particularly preferably from 1.1 to 2.1% by weight, of 3-ethyl-4-methylhexanol;
from 2.0 to 4.0% by weight, preferably from 2.2 to 3.8% by weight, particularly preferably from 2.5 to 3.5% by weight, of 2-ethyl-4-methylhexanol;
from 0.5 to 6.5% by weight, preferably from 1.5 to 6% by weight, particularly preferably from 1.5 to 5.5% by weight, of other alcohols having 9 carbon atoms;
where the total sum of the components mentioned is 100% by weight.

Such an isononanol mixture esterified with phthalic acid is present in the diisononyl phthalate of CAS No. 28553-12-0, from which the diisononyl cyclohexane-1,2-dicarboxylate having the corresponding isononyl component can be produced by hydrogenation according to the invention of the aromatic ring. Such isononanol mixtures can be obtained via dimerization of mixtures comprising predominantly n-butenes to octene mixtures by means of nickel-comprising catalysts, for example by the process of WO 95/14647, subsequent hydroformylation of the octene mixture obtained, preferably cobalt-catalyzed hydroformylation, and hydrogenation.

Very particularly preferred products of the process of the invention are selected from the group consisting of di-n-octyl cyclohexane-1,2-dicarboxylate, diisooctyl cyclohexane-1,2-dicarboxylate, di(2-ethylhexyl)cyclohexane-1,2-dicarboxylate, di-n-nonyl cyclohexane-1,2-dicarboxylate, diisononyl cyclohexane-1,2-dicarboxylate, di(2-propylheptyl)cyclohexane-1,2-dicarboxylate, di-n-decyl cyclohexane-1,2-dicarboxylate, diisodecyl cyclohexane-1,2-dicarboxylate and mixtures thereof.

Further products which are preferably obtained according to the invention are the cyclohexane-1,2-dicarboxylic esters which are disclosed in WO 99/32427 and are listed again below:
di(isononyl)cyclohexane-1,2-dicarboxylate obtainable by hydrogenation according to the invention of a di(isononyl)phthalate having the CAS No. 68515-48-0;
di(isononyl)cyclohexane-1,2-dicarboxylate obtainable by hydrogenation according to the invention of a di(isononyl)phthalate having the CAS No. 28553-12-0, based on n-butene;
di(isononyl)cyclohexane-1,2-dicarboxylate, obtainable by hydrogenation according to the invention of a di(isononyl)phthalate having the CAS No. 28553-12-0 based on isobutene;
a 1,2-di-$C_9$-ester of cyclohexanedicarboxylic acid, obtainable by hydrogenation according to the invention of a di(nonyl)phthalate having the CAS No. 68515-46-8;
a di(isodecyl)cyclohexane-1,2-dicarboxylate obtainable by hydrogenation according to the invention of a di(isodecyl)phthalate having the CAS No. 68515-49-1;
a 1,2-di(isodecyl)cyclohexanedicarboxylic ester obtainable by hydrogenation according to the invention of a di(isodecyl)phthalate which comprises mainly di(2-propylheptyl)phthalate.

Furthermore, the commercially available benzenecarboxylic esters having the trade names Jayflex DINP (CAS No. 68515-25 48-0), Jayflex DIDP (CAS No. 68515-49-1), Palatinol 9-P, Vestinol 9 (CAS No, 28553-12-0), Palatinol N (CAS No. 28553-12-0), Jayflex DIOP (CAS No. 27554-26-3), Palatinol AH (CAS No. 117-81-7) and Palatinol Z (CAS No. 26761-40-0) are also suitable starting materials for the process of the invention.

The cyclohexanepolycarboxylic acids or derivatives thereof prepared according to the invention have a lower proportion of secondary components, in particular of the secondary component hexahydrophthalide and isononyl alcohol, compared to commercially available cyclohexane-polycarboxylic acids or derivatives thereof and therefore have more advantageous use properties when used as plasticizers, for example a lower volatility and a better compatibility with plastics, for example PVC.

The present invention therefore further provides derivatives of cyclohexanepolycarboxylic acids selected from the group consisting of di-n-octyl cyclohexane-1,2-dicarboxylate, diisooctyl cyclohexane-1,2-dicarboxylate, di(2-ethylhexyl)cyclohexane-1,2-dicarboxylate, di-n-nonyl cyclohexane-1,2-dicarboxylate, diisononyl cyclohexane-1,2-dicarboxylate, di-(2-propylheptyl)cyclohexane-1,2-dicarboxylate, di-n-decyl cyclohexane-1,2-dicarboxylate, diisodecyl cyclohexane-1,2-dicarboxylate, in each case obtained by hydrogenation according to the invention, di(isononyl)cyclohexane-1,2-dicarboxylate obtainable by hydrogenation according to the invention of a di(isononyl) phthalate having the CAS No. 68515-48-0, di(isononyl)cyclohexane-1,2-dicarboxylate obtainable by hydrogenation according to the invention of a di(isononyl)phthalate having the CAS No. 28553-12-0, based on n-butene, di(isononyl) cyclohexane-1,2-dicarboxylate obtainable by hydrogenation according to the invention of a di(isononyl)phthalate having the CAS No. 28553-12-0 based on isobutene, a 1,2-di-$C_9$-ester of cyclohexanedicarboxylic acid obtainable by hydrogenation according to the invention of a di(nonyl)phthalate having the CAS No. 68515-46-8, a di(isodecyl)cyclohexane-1,2-dicarboxylate obtainable by hydrogenation according to the invention of a di(isodecyl)phthalate having the CAS No. 68515-49-1, a di(isodecyl)cyclohexane-1,2-dicarboxylate obtainable by hydrogenation according to the invention of a di(isodecyl)phthalate which comprises mainly di(2-propylheptyl)phthalate and mixtures thereof.

The at least one cyclohexanepolycarboxylic acid or derivative thereof prepared according to the invention therefore has, in a preferred embodiment, a content of hexahydrophthalide of not more than 0.06% by area, preferably less than 0.04% by area, particularly preferably from 0.01 to 0.03% by area.

The at least one cyclohexanepolycarboxylic acid or derivative thereof prepared according to the invention has, in a preferred embodiment, a content of isononanol of not more than 0.2% by area, preferably less than 0.15% by area, particularly preferably from 0.05% by area to 0.13% by area, if an isononanol ester of a cyclohexanepolycarboxylic acid is prepared.

As a result, the cyclohexanepolycarboxylic acids or derivatives thereof prepared according to the invention are particularly well suited to applications in contact with human beings, e.g. for children's toys, food packaging or medical articles, in particular as plasticizer in plastics.

The present invention therefore further provides for the use of the cyclohexanepolycarboxylic acids or derivatives thereof prepared according to the invention in applications in contact with human beings, in particular in children's toys, food packaging or in medical articles, in particular as plasticizer in plastics.

EXAMPLES

The process of the invention will now be illustrated below with the aid of some examples. Experiments 4-6 were carried out according to the invention, while experiments 1-3 are comparative experiments; in all cases, a reduction in the amount of undesirable by-products (isononanol and hexahydrophthalide) by about 50% or more is observed. Correspondingly, the content of the desired product (diisononyl cyclohexanedicarboxylate) in experiments 4-6 according to the invention is >99.5%.

Catalyst 1 is produced as described in WO2011/082991, example 1.

Catalyst 2 (comparison) is produced as described in DE19624485, production example.

Hydrogenation Examples

The hydrogenations are carried out in a cascade made up of 8 tubes (internal diameter 6 mm, length 150 cm). Here, the first six tubes are operated in series as main reactor with recirculation, i.e. the output from the sixth tube was partly recirculated to the first tube. The last 2 tubes were operated in a single pass as after-reactor. Each tube was charged with 30 ml of catalyst.

The hydrogenation was carried out using pure hydrogen. The feed was selected so that the space velocity over the catalyst in the main reactor (kg(diisonyl phthalate)/(l(catalyst)·h) achieved the value indicated in the table below. The recirculation ratio was selected so that the superficial velocity in the main reactor is as indicated in table 1. The hydrogen was introduced under pressure regulation at the pressure indicated in table 1. The reaction temperatures are likewise indicated in table 1.

TABLE 1

Hydrogenation experiments

| No. | Cat. | Space velocity over the catalyst [kg/(l · h)] | Superficial velocity [m/h] | T in the main reactor [° C.] | T in the after-reactor [° C.] | Pressure [bar] |
|---|---|---|---|---|---|---|
| 1 | 2 (comp.) | 0.5 | 55 | 111 | 125 | 240 |
| 2 | 1 | 0.73 | 55 | 126 | 155 | 240 |
| 3 | 1 | 0.5 | 55 | 111 | 125 | 240 |
| 4 | 1 | 0.5 | 34 | 111 | 125 | 36 |
| 5 | 1 | 0.5 | 34 | 120 | 140 | 36 |
| 6 | 1 | 0.25 | 34 | 111 | 125 | 36 |

Space velocity over the catalyst: kg (diisononyl phthalate)/(l(catalyst) hour)
Superficial velocity: $m^3$(diisononyl phthalate)/($m^2$(reactor cross section)/time (h))

TABLE 2

Results of the hydrogenation experiments

GC method:
Column: DB-1 30 m, ID 0.32 mm, FD 0.25 μm
Temperature program: 50° C., 4 min - 5° C./min - 290° C. - 28 min
Injection volume: 1 μl
Inlet temperature: 300° C., detector temperature (FID): 300° C.
Isononanol: 13-18 min
Hexahydrophthalide: 20 min
Diisononyl cyclohexane-1,2-dicarboxylate (DINCH): 47-54 min

| No. | Isononanol [GC-% by area] | Hexahydro-phthalide [GC-% by area] | DINCH content [GC-% by area] | Total others [GC-% by area] |
|---|---|---|---|---|
| 1 | 0.073 | 0.449 | 99.2 | 0.278 |
| 2 | 0.776 | 0.181 | 98.6 | 0.443 |
| 3 | 0.077 | 0.282 | 99.4 | 0.241 |
| 4 | 0.019 | 0.097 | 99.7 | 0.184 |
| 5 | 0.028 | 0.109 | 99.6 | 0.263 |
| 6 | 0.029 | 0.113 | 99.7 | 0.158 |

The invention claimed is:
1. A process for preparing at least one cyclohexanepolycarboxylic acid or a derivative thereof by bringing at least one corresponding benzenepolycarboxylic acid or a derivative thereof into contact with a hydrogen-comprising gas in the presence of at least one coated catalyst comprising an active metal selected from the group consisting of ruthenium, rhodium, palladium, platinum and mixes thereof applied to a support material comprising silicon dioxide, where the support material has a pore volume of from 0.6 to 1.0 ml/g, determined by Hg porosimetry, a BET surface from 280 to 500 $m^2/g$, and at least 90% of the pores present have a diameter of from 6 to 12 nm, wherein the contacting is carried out at a superficial velocity of not more than 50 m/h.

2. The process according to claim 1, wherein the process is carried out at a superficial velocity of not more than 45 m/h.

3. The process according to claim 1, wherein the process is carried out at a superficial velocity of not more than 40 m/h.

4. The process according to claim 1, wherein the contacting is carried out at a temperature of from 50 to 250° C., preferably from 70 to 180° C., and a pressure above 10 bar, preferably in the range from 20 to 80 bar, particularly preferably from 30 to 50 bar.

5. The process according to claim 1, wherein the contacting is carried out at a temperature of from 70 to 180° C., and a pressure in the range from 20 to 80 bar.

6. The process according to claim 4, wherein the contacting is carried out at a pressure from 30 to 50 bar.

7. The process according to claim 1, wherein the at least one derivative of the benzenepolycarboxylic acid is a monoester, diester, triester, tetraester or anhydride of the benzenepolycarboxylic acid.

8. The process according to claim 1, wherein the at least one derivative of a benzenepolycarboxylic acid is a monoester, diester, triester or tetraester of the benzenepolycarboxylic acid, which ester has been obtained by reaction with a nonanol mixture in which from 0 to 20% by weight of the nonanol mixture have no branching, from 5 to 90% by weight, have one branching point, from 5 to 70% by weight, have two branching points, from 0 to 10% by weight have three branching points and from 0 to 40% by weight, are other components, wherein the sum of the components mentioned does not exceed 100% by weight.

9. The process according to claim 1, wherein the at least one derivative of a benzenepolycarboxylic acid is a monoester, diester, triester or tetraester of the benzenepolycarboxylic acid, which ester has been obtained by reaction with a nonanol mixture in which from 0.5 to 18% by weight of the nonanol mixture have no branching, from 10 to 80% by weight have one branching point, from 10 to 60% by weight have two branching points, from 0 to 8% by weight have three branching points and from 0.1 to 30% by weight are other components, wherein the sum of the components mentioned does not exceed 100% by weight.

10. The process according to claim 1, wherein the at least one derivative of a benzenepolycarboxylic acid is a monoester, diester, triester or tetraester of the benzenepolycarboxylic acid, which ester has been obtained by reaction with a nonanol mixture in which from 6 to 16% by weight of the nonanol mixture have no branching, from 45 to 75% by weight have one branching point, from 15 to 35% by weight have two branching points, from 0 to 4% by weight have three branching points and from 0.5 to 6.5% by weight are other components, wherein the sum of the components mentioned does not exceed 100% by weight.

* * * * *